United States Patent [19]

Sinskey

[11] Patent Number: 4,601,720

[45] Date of Patent: Jul. 22, 1986

[54] INTRAOCULAR LENS ASSEMBLY

[76] Inventor: Robert M. Sinskey, 2232 Santa Monica Blvd., Santa Monica, Calif. 90404

[21] Appl. No.: 236,689

[22] Filed: Feb. 24, 1981

[51] Int. Cl.$^4$ .............................................. A61F 2/16
[52] U.S. Cl. ................................................... 623/6
[58] Field of Search ........................... 3/13, 1; 623/6

[56] References Cited

U.S. PATENT DOCUMENTS

| | | | |
|---|---|---|---|
| 2,834,023 | 5/1958 | Lieb | 3/13 X |
| 3,866,249 | 2/1975 | Flom | 3/13 |
| 4,014,049 | 3/1977 | Richards et al. | 3/13 |
| 4,087,866 | 5/1978 | Choyce et al. | 3/13 |
| 4,159,546 | 7/1979 | Shearing | 3/13 |
| 4,242,760 | 1/1981 | Rainin | 3/13 |
| 4,244,060 | 1/1981 | Hoffer | 3/13 |
| 4,251,887 | 2/1981 | Anis | 3/13 |
| 4,366,582 | 1/1983 | Faukner | 623/6 |

OTHER PUBLICATIONS

Pseudophakos (Book) by N. S. Jaffe et al, The C. V. Mosby Co. (publisher) 1978, pp. 37-40; the Strampelli Lens shown in FIG. 4-5.
"The Intraocular Implant Lens Development and Results with Special Reference to the Binkhorst Lens" by M. E. Nordlohne (Book), second edition, The Williams & Wilkins Co. Baltimore, 1975, pp. 14-20.
"Experience with Twelve Cases of Intra-Ocular Anterior Chamber Implants for Aphakia" by J. Boberg-Ans, British Journal of Ophthalmology, vol. 45, No. 1, Jan. 1961, pp. 37-43.

Primary Examiner—Ronald L. Frinks
Attorney, Agent, or Firm—Harris, Kern, Wallen & Tinsley

[57] ABSTRACT

An intraocular lens assembly including an intraocular lens with first and second generally U-shaped flexible fingers carried on and projecting from the lens in opposite directions, with each of the fingers having a continuous curve from the lens to the outermost portion of the finger and preferably to the end of the finger. The lens typically is plano-convex with a cylindrical edge with the fingers projecting outward from the edge, preferably at a small angle to the planar surface of the lens.

6 Claims, 3 Drawing Figures

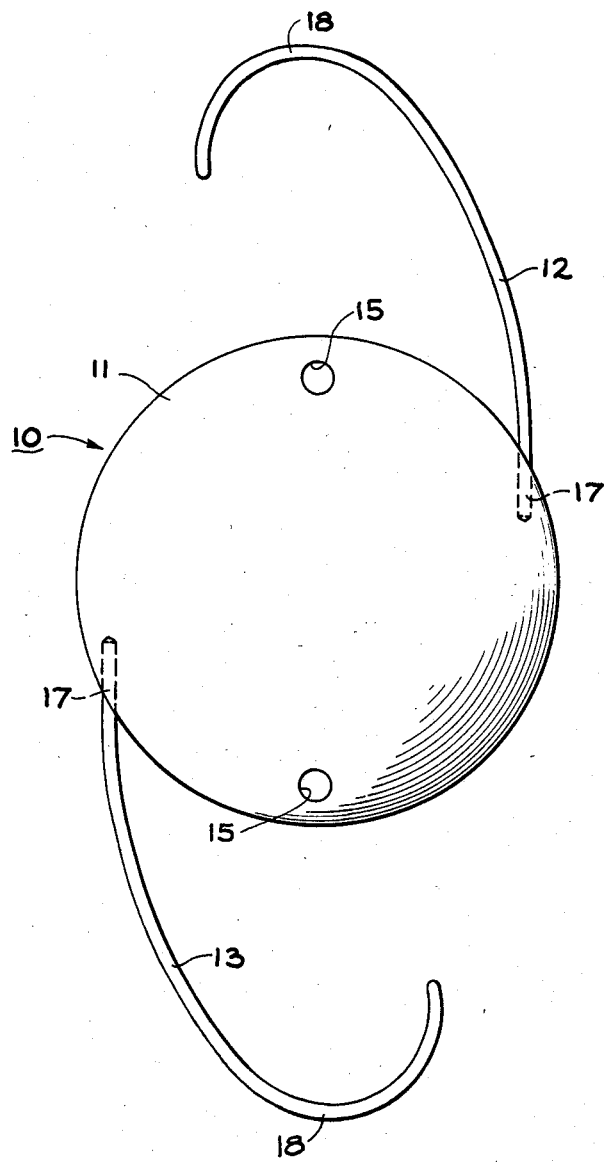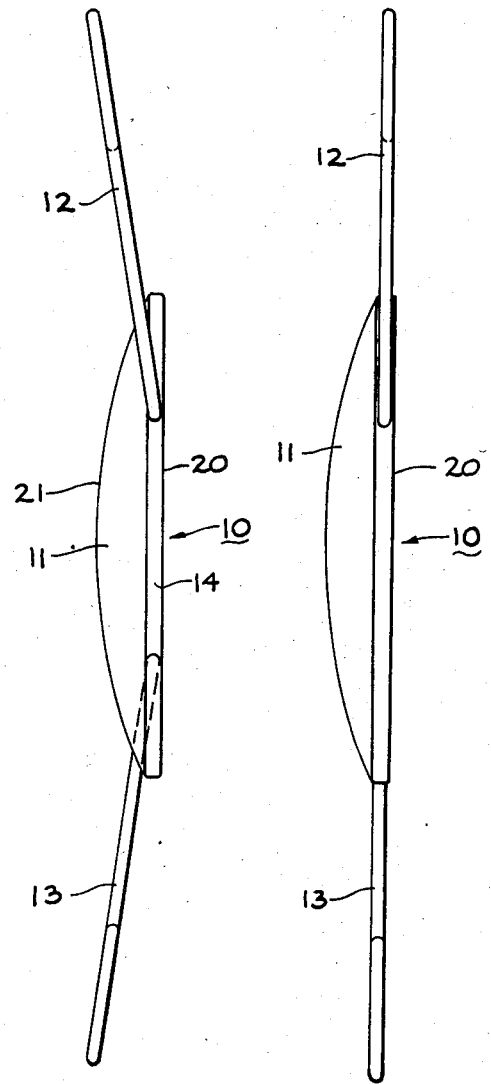
FIG. 1　　　　FIG. 2　　FIG. 3

INTRAOCULAR LENS ASSEMBLY

BACKGROUND OF THE INVENTION

This invention relates to intraocular lens of the general type sometimes referred to as a Shearing intraocular lens.

The conventional lens typically is a plano-convex lens with a generally cylindrical edge or rim, with J-shaped fingers projecting outward from the rim in opposite directions. These fingers serve to position the lens in the eye of the wearer. While the fingers are curved in the outer portions, the major portion of each finger is straight, resulting in what is referred to as a J-shaped finger. Because of this straight configuration, these fingers are relatively stiff and sometimes result in a rupture of the posterior capsule when being implanted, and a dropping down of the lens postoperatively.

Accordingly, it is an object of the present invention to provide a new and improved intraocular lens assembly incorporating a more flexible finger construction which will serve to position the lens while reducing the likelihood of damage to the eye.

It is a particular object of the invention to provide such an intraocular lens assembly incorporating generally U-shaped flexible fingers with each of the fingers having a continuous curve from the lens at least to the outermost portion of the finger.

These and other objects, advantages, features and results will more fully appear in the course of the following descriptions.

SUMMARY OF THE INVENTION

The intraocular lens assembly of the invention comprises an intraocular lens which may be conventional in construction, and first and second generally U-shaped flexible fingers carried on and projecting from the lens in opposite directions, with each of the fingers having a continuous curve from the lens at least to the outermost portion of the finger giving the fingers the desired flexibility. In a perferred embodiment, the fingers are positioned at an angle to the plane of the lens, angled toward the convex surface of the lens preferably in the range of about 7 to about 15 degrees and usually in the order of 10 degrees.

BRIEF DESCRIPTION OF THE DRAWING

FIG. 1 is a front view of an intraocular lens incorporating the presently preferred embodiment of the invention;

FIG. 2 is a side view of the lens of FIG. 1; and

FIG. 3 is a view similar to that of FIG. 2 showing an alternative embodiment of the lens.

DESCRIPTION OF THE PREFERRED EMBODIMENTS

The intraocular lens assembly 10 as shown in FIGS. 1 and 2 is utilized as a replacement lens for the human eye. The lens assembly includes a lens 11 and flexible fingers 12, 13.

The lens 11 may be conventional in construction and typically is formed of polymethylmethacrylate with a plano-convex configuration. The lens usually has a rim or edge 14 which is generally cylindrical and may have rounded corners. The small openings 15 may be provided through the lens to provide locations for manipulation tools.

The flexible fingers 12, 13 have the same configuration and construction, and typically are formed of a plastic such as polypropylene, and typically are in the order of 0.15 millimeters diameter. The fingers are inserted into openings 17 in the rim of the lens and typically are held in place by heat staking.

Each of the fingers is shaped to have to continuous curve from the point where the finger emerges from the lens to at least the outermost portion 18 of the finger, and preferably all the way to the free end of the finger. As is readily see from FIG. 1 of the drawing, in each of the fingers the inner portion adjacent the fixed end at the opening 17 has a longer radius than the outer portion adjacent the free end, with the free end directed toward the lens. In the preferred embodiment illustrated, the radius of the inner portion is more than twice the radius of the outer portion, with the free end of the finger directed toward the central portion of the lens. This is in contrast to the earlier designs where the fingers are J-shaped with a long straight section which terminates in a curve at the free end. The continuous curve configuration of the present invention results in a substantially more flexible finger, even when the prior art finger and the finger of the present invention are made of the same material and the same size. With this flexible configuration, the likelihood of rupture of the posterior capsule when implanting the lens assembly is substantially reduced.

In the preferred embodiment illustrated in FIGS. 1 and 2, the fingers 12, 13 are postioned at an angle to the planar surface 20 of the lens, toward the convex surface 21 of the lens, as best seen in FIG. 2. The angle between the finger and the planar surface preferably is in the range of about 7 degrees to about 15 degrees, and it has been found that an angle in the order of 10 degrees is satisfactory for most patients. The forward angling of the fingers holds the lens more posterior to decrease the incidence of touching the iris to the optic and/or allowing the iris to get behind the optic of the lens.

An alternative configuration with the fingers 12, 13 in a plane parallel to the planar surface 20 of the lens, is shown in FIG. 3. Otherwise the embodiment of FIG. 3 is the same as the embodiment of FIGS. 1 and 2.

Typically a lens is in the order of 6 millimeters diameter, and the overall dimension of the lens assembly at the outermost portion 18 may be made greater than with the prior lens assemblies. Typically this dimension is now 13.5 millimeters whereas in the prior art devices it was 13.0 millimeters. While this difference is not large, it is significant in that it permits use of the lens assembly with the flexible fingers in a wider range of patients while resulting in proper positioning of the lens in the eye.

I claim:

1. An intraocular lens assembly comprising in combination:

an intraocular lens for implantation in the posterior chamber of a human eye; and first and second generally U-shaped flexible fingers carried on and projecting away from said lens in opposite directions away from each other, each of said fingers having a continuous curve from said lens at least to the outermost portion of the finger as viewed from the front of said lens, each of said fingers having a fixed end and a free end, with said fixed end joined to said lens and with said free end spaced from said lens, each of said fingers having a first portion adjacent said fixed end and a second portion adjacent said free end, with said first portion of longer radius and said second portion of shorter radius, with said free end directed inward toward said lens.

2. A lens assembly as defined in claim 1 wherein said lens is plano-convex with a cylindrical edge, and each of said fingers projects outward from said edge at an angle to the plane of said lens toward the convex surface of said lens.

3. A lens assembly as defined in claim 2 wherein said angle is in the range of about 7 degrees to about 15 degrees.

4. A lens assembly as defined in claim 2 wherein said angle is in the order of 10 degrees.

5. A lens assembly as defined in claim 1 wherein said lens is plano-convex with a cylindrical edge, and each of said fingers projects outward from said edge in a plane substantially parallel to the planar surface of the said lens.

6. A lens assembly as defined in claim 1 wherein said radius of said first portion is at least twice that of said second portion, with said free end directed toward the central portion of said lens.

* * * * *